(12) United States Patent
Blomberg

(10) Patent No.: US 11,141,554 B2
(45) Date of Patent: *Oct. 12, 2021

(54) REGULATION OF DELIVERY OF MULTIPLE ANESTHETIC AGENTS TO A PATIENT FROM AN ANESTHETIC BREATHING APPARATUS

(71) Applicant: MAQUET CRITICAL CARE AB, Solna (SE)

(72) Inventor: Urban Blomberg, Linkoeping (SE)

(73) Assignee: MAQUET CRITICAL CARE AB, Solna (SE)

( * ) Notice: Subject to any disclaimer, the term of this patent is extended or adjusted under 35 U.S.C. 154(b) by 1356 days.

This patent is subject to a terminal disclaimer.

(21) Appl. No.: 14/790,361

(22) Filed: Jul. 2, 2015

(65) Prior Publication Data

US 2015/0297857 A1 Oct. 22, 2015

Related U.S. Application Data

(62) Division of application No. 12/742,481, filed as application No. PCT/EP2007/062228 on Nov. 12, 2007, now Pat. No. 9,095,678.

(51) Int. Cl.
*A61M 16/10* (2006.01)
*A61M 16/01* (2006.01)
(Continued)

(52) U.S. Cl.
CPC .......... *A61M 16/104* (2013.01); *A61M 16/01* (2013.01); *A61M 16/021* (2017.08); *A61M 16/022* (2017.08); *A61M 16/18* (2013.01); *A61M 16/0075* (2013.01); *A61M 16/0078* (2013.01); *A61M 16/0081* (2014.02);
(Continued)

(58) Field of Classification Search
CPC .............. A61M 16/00; A61M 16/0003; A61M 16/0051; A61M 16/009; A61M 16/0093; A61M 16/01; A61M 16/021; A61M 16/022; A61M 16/024; A61M 16/10; A61M 16/1005; A61M 16/104; A61M 16/12; A61M 16/122; A61M 2016/102; A61M 2016/1035; A61M 2202/0085; A61M 2202/0241; A61M 2202/0291;
(Continued)

(56) References Cited

U.S. PATENT DOCUMENTS 4,989,597 A 2/1991 Werner
5,094,235 A 3/1992 Westenskow et al.
(Continued)

OTHER PUBLICATIONS

First Office Action dated Jul. 26, 2012, issued in Chinese Application No. 200780102212.9 (3 pages).
(Continued)

*Primary Examiner* — Colin W Stuart

(57) ABSTRACT

In a method and system of regulating multiple anesthetic agents in a breathing circuit of an anesthetic breathing apparatus is disclosed, a primary anesthetic agent added to the breathing circuit is regulated to a set desired value of the amount of the primary anesthetic agent, and a secondary anesthetic agent in the breathing circuit is regulated to an amount of said secondary anesthetic agent that it is equal to or less than a defined threshold level, e.g. of the concentration, of the secondary anesthetic agent.

15 Claims, 7 Drawing Sheets

(51) Int. Cl.
*A61M 16/00* (2006.01)
*A61M 16/18* (2006.01)
*A61M 16/22* (2006.01)

(52) U.S. Cl.
CPC ......... *A61M 16/0093* (2014.02); *A61M 16/22* (2013.01); *A61M 2016/0027* (2013.01); *A61M 2016/0042* (2013.01); *A61M 2016/1035* (2013.01); *A61M 2205/52* (2013.01); *A61M 2230/437* (2013.01)

(58) Field of Classification Search
CPC .... A61M 2202/048; A61M 2205/3327; A61M 2205/3379; A61M 2230/437
See application file for complete search history.

(56) References Cited

U.S. PATENT DOCUMENTS

| | | | |
|---|---|---|---|
| 5,237,990 | A | 8/1993 | Psaros et al. |
| 5,537,992 | A | 7/1996 | Bjoernstigerna et al. |
| 5,649,531 | A | 7/1997 | Heinonen |
| 5,699,788 | A | 12/1997 | Lekholm et al. |
| 5,769,072 | A | 6/1998 | Olsson et al. |
| 5,771,882 | A | 6/1998 | Psaros et al. |
| 5,931,161 | A | 8/1999 | Keilbach et al. |
| 6,046,453 | A | 4/2000 | Gingrich et al. |
| 6,216,690 | B1 * | 4/2001 | Keitel ................ A61M 16/104 128/203.12 |
| 6,220,242 | B1 | 4/2001 | Wallin |
| 6,289,891 | B1 | 9/2001 | Cewers |
| 6,422,073 | B1 | 7/2002 | Krahbichler et al. |
| 6,634,355 | B2 | 10/2003 | Colas |
| 7,556,036 | B2 | 7/2009 | Bouillon et al. |
| 7,836,882 | B1 * | 11/2010 | Rumph ................ G16H 40/63 128/203.12 |
| 7,987,848 | B2 | 8/2011 | Dammann |
| 7,997,268 | B1 | 8/2011 | Leonard et al. |
| 2004/0250814 | A1 | 12/2004 | Post et al. |
| 2006/0090757 | A1 | 5/2006 | Dittmann |
| 2006/0278220 | A1 | 12/2006 | Schermeier et al. |
| 2007/0089741 | A1 * | 4/2007 | Bohm ................ A61M 16/01 128/203.12 |
| 2007/0125377 | A1 * | 6/2007 | Heinonen ............ A61M 16/20 128/204.21 |
| 2007/0278110 | A1 | 12/2007 | Jafari |
| 2008/0011294 | A1 * | 1/2008 | Heesch ............ A61M 16/0051 128/200.24 |

OTHER PUBLICATIONS

Second Office Action dated Apr. 23, 2013, issued in Chinese Application No. 200780102212.9 (3 pages).
Third Office Action dated Aug. 3, 2013, issued in Chinese Application No. 200780102212.9 (4 pages).
Fourth Office Action dated Feb. 19, 2014, issued in Chinese Application No. 200780102212.9 (4 pages).
Office Action issued in EP Application No. 15170967.2 dated Nov. 26, 2015 (6 pages).

* cited by examiner

REGULATION OF DELIVERY OF MULTIPLE ANESTHETIC AGENTS TO A PATIENT FROM AN ANESTHETIC BREATHING APPARATUS

RELATED APPLICATION

The present application is a divisional application of U.S. application Ser. No. 12/742,481, having an official filing date of Sep. 21, 2010, the content of which is incorporated herein by reference.

BACKGROUND OF THE INVENTION

Field of the Invention

This invention pertains in general to the field of delivery of volatile liquid anesthetic agents by means of an anesthetic breathing apparatus. More particularly the invention relates to a control method and system in an anesthetic breathing apparatus when multiple anesthetic agents are present in a breathing circuit of the anesthetic breathing apparatus to which a patient is fluidly connected via its airways.

Description of the Prior Art

During anesthesia, the patient is usually supplied with a gas mixture containing nitrous oxide, oxygen and an anesthetic agent. Generally, one of the volatile anesthetic agents desflurane, enflurane, isoflurane, halothane or sevoflurane is the anesthetic employed. These are all liquid at normal room temperature.

A liquid volatile anesthetic agent administered to the patient via its airways is therefore vaporized in an anesthetic vaporizer that is fluidly connected to a breathing circuit of an anesthetic breathing apparatus, such as an anesthesia machine. The vaporized anesthetic agent is conveyed to the breathing circuit with a flow of fresh gas that is suitably controlled. The patient in turn is fluidly connected to the breathing circuit via a suitable tubing.

The breathing circuit of the anesthetic breathing apparatus is usually, of economical reasons, operated such that the patient re-breathes exhalation gases after $CO_2$ is removed in a $CO_2$ absorber, and the $O_2$ level in the inhalation gases is adjusted by replenishing the latter in the breathing circuit. The above mentioned fresh gas flow is kept much lower than the patient gas flow from and to the breathing circuit. Thus it is ensured that only a minimum of liquid anesthetic is exhausted from the anesthetic breathing apparatus, e.g. to a gas evacuation system.

A mixing of different anesthetic agents is attempted to be avoided, as pharmacological summation effects thereof are still not fully understood and may vary from one patient to another. For instance in U.S. Pat. No. 6,289,891 a safety system is disclosed that avoids mixing of different anesthetic agents in an anesthetic vaporizer of an anesthetic breathing apparatus.

However, under certain operating conditions of the anesthetic breathing apparatus, it might still occur that more than one anesthetic agent is present in the breathing circuit. For instance, an anesthetic breathing apparatus may comprise a number of anesthetic vaporizers. Multiple anesthetic agents might exist for instance in a transition phase when switching between two different anesthetic agents delivered from two anesthetic vaporizers of the anesthetic breathing apparatus, each delivering a different anesthetic agent. For instance a first anesthetic agent may be provided from a first anesthetic vaporizer during an induction phase of anesthesia. Subsequently, in order to maintain the level of anesthesia established by the first anesthetic agent, a second anesthetic agent may be delivered to the breathing circuit and therefrom to the patient from a second anesthetic vaporizer. This might also be desired if a patient shows symptoms of not tolerating a certain anesthetic agent, e.g. due to allergic reactions. In cases like this, multiple anesthetic agents may be present in the breathing circuit, at least for a certain time, for instance when operating the anesthetic breathing apparatus with low fresh gas flows into the breathing circuit.

Usually, in order to avoid that multiple anesthetic agents are present in the breathing circuit, the latter may be flushed for removing all anesthetic agents as fast as possible therefrom. Then a new anesthetic agent will be provided with a rather high gas flow to replenish the breathing circuit with the new anesthetic agent. Thus, the patient will not significantly loose depth of anesthesia during this flush and replenish procedure, as sufficient anesthetic agent is dissolved in the patient's blood serving as a depot until new anesthetic agent is provided to the patient. On the other hand, the breathing circuit, that has been flushed and replenished with the new anesthetic agent, will receive a certain amount of the accumulated anesthetic agent from the patient with exhalation gases comprising anesthetic agent dissolved from the blood of the patient. This includes the previous anesthetic agent, whereby the concentration thereof in the breathing circuit will increase again for a certain time after the flush and replenish procedure, until the previous anesthetic agent is washed out from the breathing circuit or eventually consumed by the patient. Hence, the change from one anesthetic agent to another anesthetic agent supplied to a patient may be time consuming and involve mixtures of multiple anesthetic agents in the breathing circuit that are not known or not desired. One way to accelerate removal of the previous anesthetic agent would be to regularly repeat the flush and replenish procedure. However, the flush and replenish procedure is not desired from an economical point of view as a large amount of anesthetic agent is wasted from the anesthetic breathing apparatus to the exhaust thereof during such a procedure.

In addition, if for instance due to the human factor safety locks to activate more than one vaporizer at a time are overridden, it may also occur that a mixture of several anesthetic agents are delivered to the patient.

Thus, there is a need for an improved system and/or method for providing or regulating a plurality of anesthetic agents in a breathing circuit, e.g. without impairing patient safety.

Hence, an improved anesthetic breathing apparatus would be advantageous, and in particular an anesthetic breathing apparatus allowing for increased flexibility, and/or cost-effectiveness, and/or patient safety, with regard to multiple anesthetic agents in a breathing circuit thereof would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a method, system and computer program according to the appended patent claims.

According to one aspect of the invention, a method of regulating multiple anesthetic agents in a breathing circuit of an anesthetic breathing apparatus is provided. The method includes regulating at least one primary anesthetic agent added to the breathing circuit to a set dose of the primary anesthetic agent, and regulating at least one secondary anesthetic agent present in the breathing circuit, to a dose of the secondary anesthetic agent that it is equal to or less than a defined dose of the secondary anesthetic agent by controlling a ratio of re-breathed gas and fresh gas in the breathing circuit, or by controlling a ratio of re-breathed secondary anesthetic agent and primary anesthetic agent.

According to another aspect of the invention, a system in an anesthetic breathing apparatus, for regulating multiple anesthetic agents in a breathing circuit of said anesthetic breathing apparatus is provided. The system includes a unit configured for regulating at least one primary anesthetic agent added to said breathing circuit to a set dose of said primary anesthetic agent, and regulating at least one secondary anesthetic agent present in the breathing circuit, to a dose of the secondary anesthetic agent that it is equal to or less than a defined dose of the secondary anesthetic agent by controlling a ratio of re-breathed gas and fresh gas in the breathing circuit, or by controlling a ratio of re-breathed secondary anesthetic agent and primary anesthetic agent.

According to a further aspect of the invention, a computer program for regulating multiple anesthetic agents in a breathing circuit of an anesthetic breathing apparatus, executable in a computing device thereof is provided. The computer program has a first code segment for regulating at least one primary anesthetic agent added to the breathing circuit to a set dose of the primary anesthetic agent, and a second code segment for regulating at least one secondary anesthetic agent present in the breathing circuit, to a dose of the secondary anesthetic agent that it is equal to or less than a defined dose of the secondary anesthetic agent, by controlling a ratio of re-breathed gas and fresh gas in the breathing circuit, or by controlling a ratio of re-breathed secondary anesthetic agent and primary anesthetic agent.

Some embodiments of the invention provide for an improved economic use of anesthetic agents in an anesthetic breathing apparatus.

Some embodiments of the invention provide for dealing with the issue of mixed anesthetic agents when starting up an anesthetic breathing apparatus with unknown history.

DESCRIPTION OF THE PREFERRED EMBODIMENTS

Figure 1:
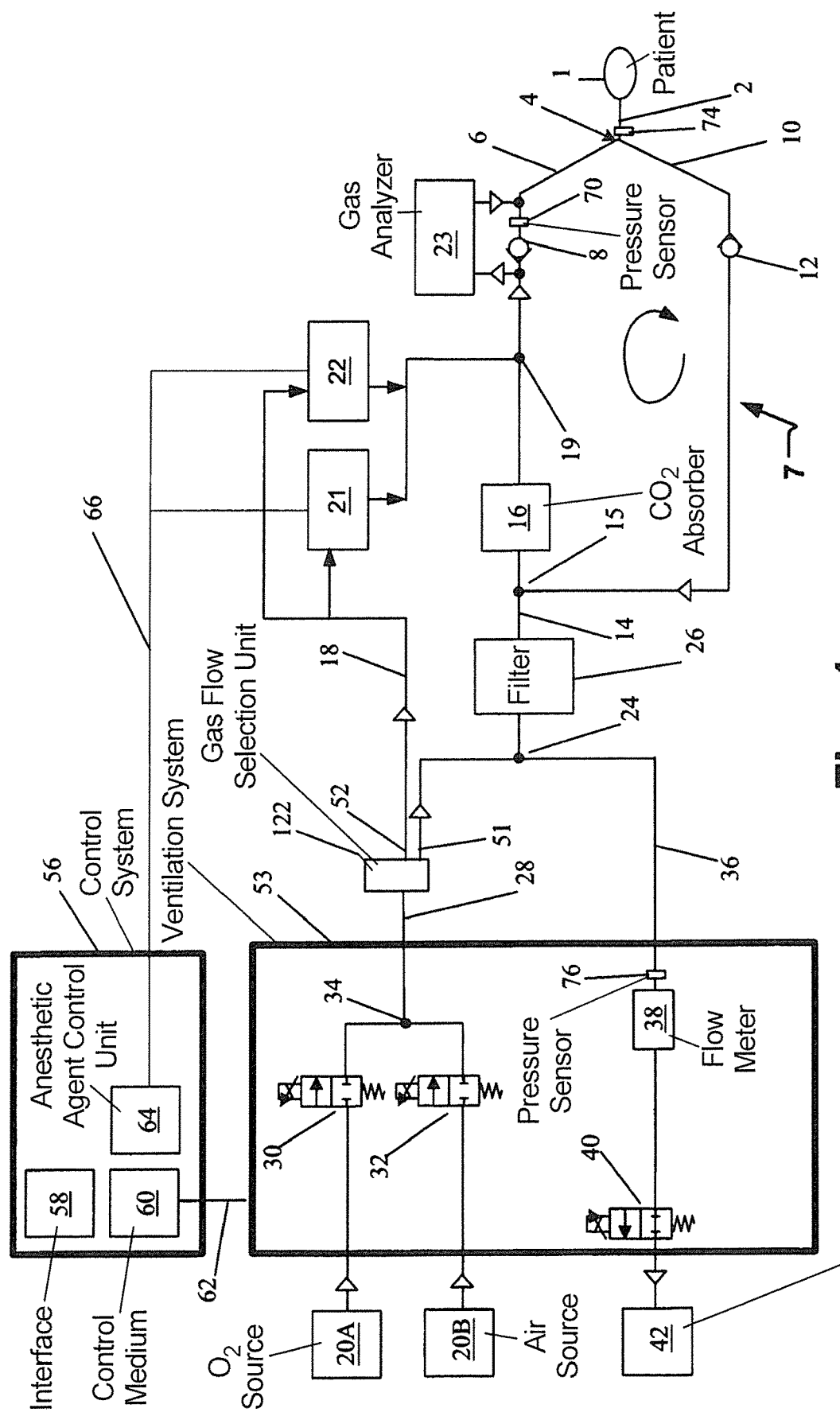
FIG. 1 is a schematic drawing of an anesthetic breathing apparatus.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The term "dose", as used in the context of the present application, is a specific quantity or concentration of a drug or agent taken or administered at any one time or at least at one specified interval.

The following description focuses on embodiments of the present invention applicable to anesthesia machines. However, it will be appreciated that the invention is not limited to this application but may be applied to many other anesthetic breathing apparatus, including for example an intensive care ventilator with added anesthetic breathing circle and anesthetic vaporizers.

An embodiment of the control method includes:

a) Regulating a primary/new anesthetic agent added to a breathing circuit in such a manner that the concentration of the primary anesthetic agent, AA1, is adjusted to a set desired value of the concentration of the primary anesthetic agent, setAA1:

$$AA1 = setAA1,$$

and b) regulating the concentration of a secondary agent, AA2, which is an anesthetic agent that previously was fed into the breathing circuit, in such a manner that it is equal to or less than a defined threshold level of the concentration of the secondary anesthetic agent, MAX_AA2:

$$AA2 <= MAX\_AA2.$$

In embodiments, regulating a concentration of an anesthetic agent in an anesthetic breathing apparatus, e.g. in a breathing circle thereof, may be implemented by a closed loop, feedback controlled regulation comprising an gas analyzer providing a concentration of anesthetic agents in the breathing circle as a control parameter, amongst other parameters known in the art.

In this manner, the re-breathing of the secondary (i.e. previously used) anesthetic agent is reduced.

It should be noted that the terms "primary" and "secondary" do not exclude and may comprise, at least in certain phases of regulation, that a "secondary" agent is present in a breathing circuit in an absolute, relative, or dosage related amount that is higher than the absolute, relative, or dosage related amount of a "primary" agent in the breathing circuit. The terms "primary" and "secondary" only relate to the method of regulating described herein.

Embodiments of the present method provide for an improved economic use of anesthetic agents in an anesthetic breathing apparatus. A first anesthetic agent already present in a breathing circle (=secondary anesthetic agent) is used optimally for anesthesia of a patient fluidly connected to the breathing circuit, when transitioning to, or adding a second, or further, anesthetic agent (=primary/new anesthetic agent) to the breathing circuit. This is made under the provision that an effect of mixed anesthetic agents is on a controlled level on which patient safety is ensured.

An automatic function for limiting the effect of mixed anesthetic agents to a desired level is provided while maintaining a maximum re-breathing of gas by the patient from the patient circuit.

Embodiments of the present method also provide for dealing with the issue of mixed anesthetic agents when starting up an anesthetic breathing apparatus with unknown history. Starting up an anesthetic breathing apparatus with unknown history may be desired in emergency situations, e.g. for taking immediate care of a patient. In this case, the anesthetic breathing apparatus may not be brought into a well defined condition, e.g. by a pre-use check, and an anesthetic agent may perhaps be present in the breathing circuit from a previous operation of the anesthetic breathing apparatus. In this case, the automatic function for limiting the effect of mixed anesthetic agents to a desired level may be provided while maintaining a maximum re-breathing of gas by the patient from the patient circuit. More precisely, a first anesthetic agent (=secondary anesthetic agent) may be present in the breathing circuit at start-up. This first anesthetic agent is detected by means of an anesthetic gas analyzer comprised in the anesthetic breathing apparatus. In case medical personal activates an anesthetic vaporizer with a second anesthetic agent (=primary anesthetic agent), different from the first anesthetic agent, the first anesthetic agent is still utilized for anesthesia of the patient. Re-breathing of the first anesthetic agent is maintained and topped up with the second anesthetic agent. Even in this case, the condition is observed that an effect of mixed anesthetic agents is on a controlled level.

One example when the present method is of benefit is when changing from a first anesthetic agent to a second anesthetic agent under operation of the anesthesia breathing circuit. Hitherto the patient has been supplied with a flow of gas comprising an unknown or undefined mixture of different anesthetic agents, which may have lead to unpredictable, perhaps disadvantageous, summation effects of the mixed anesthetic agents.

A requirement for implementing embodiments of the present control method is that a variable and/or controllable degree of re-breathing of anesthetic agent is able to be provided by the anesthetic breathing apparatus, i.e. which amount of anesthetic agent is re-circulated to the patient in the breathing circuit.

Another prerequisite is that the delivery of anesthetic agent to the breathing circuit is variable and/or controllable.

A further requirement for implementing embodiments of the control method is at least one anesthetic gas analyzer that is capable of measuring concentrations of a plurality of anesthetic agents simultaneously or in parallel. The anesthetic gas analyzer needs to be capable of measuring concentrations of all the different anesthetic agents that are present in the breathing circuit at a given point in time. One integral gas analyzer or a number of anesthetic gas analyzers may be present in the anesthetic breathing apparatus for this task.

Some anesthetic breathing apparatuses, and sections thereof, enabling this requirements are described below, e.g. with reference to FIG. 1, 2, and FIGS. 6a to 6c.

Anesthetic vaporizers that may be used for implementing the invention comprise any anesthetic vaporizer which has an electronically controllable output concentration of vaporized anesthetic agent. Such anesthetic vaporizers include injection based anesthetic vaporizers, but also evaporation based vaporizers. Electronically controlling of the output concentration of vaporized anesthetic agent comprises also electrically adjusting mechanical concentration selection units, e.g. by rotating a concentration selector dial by means of an electronically controlled actuating device, such as a stepping motor. A number of different kinds of such anesthetic vaporizers are described in the literature and are well known to those skilled in the art. Since details of the vaporizer design and function are not of essential relevance to the present invention, they need not be specified below.

Anesthetic gas analyzers measuring concentrations of two or more anesthetic agents simultaneously are a prerequisite for the method described herein. Such anesthetic gas analyzers are commercially available, e.g. the Artema AION™ multigas analyzer Artema AB, and need not be specified further detailed. Such anesthetic gas analyzers are for instance capable of identifying, measuring and monitoring all anesthetic agents that may be provided in the breathing circuit, e.g. the five anesthetic agents mentioned above. In addition gas concentrations of $CO_2$, $N_2O$ and $O_2$ may be measured, e.g. by a paramagnetic measurement device, such as the commercially available ServoMex gas measurement device.

Figure 2:
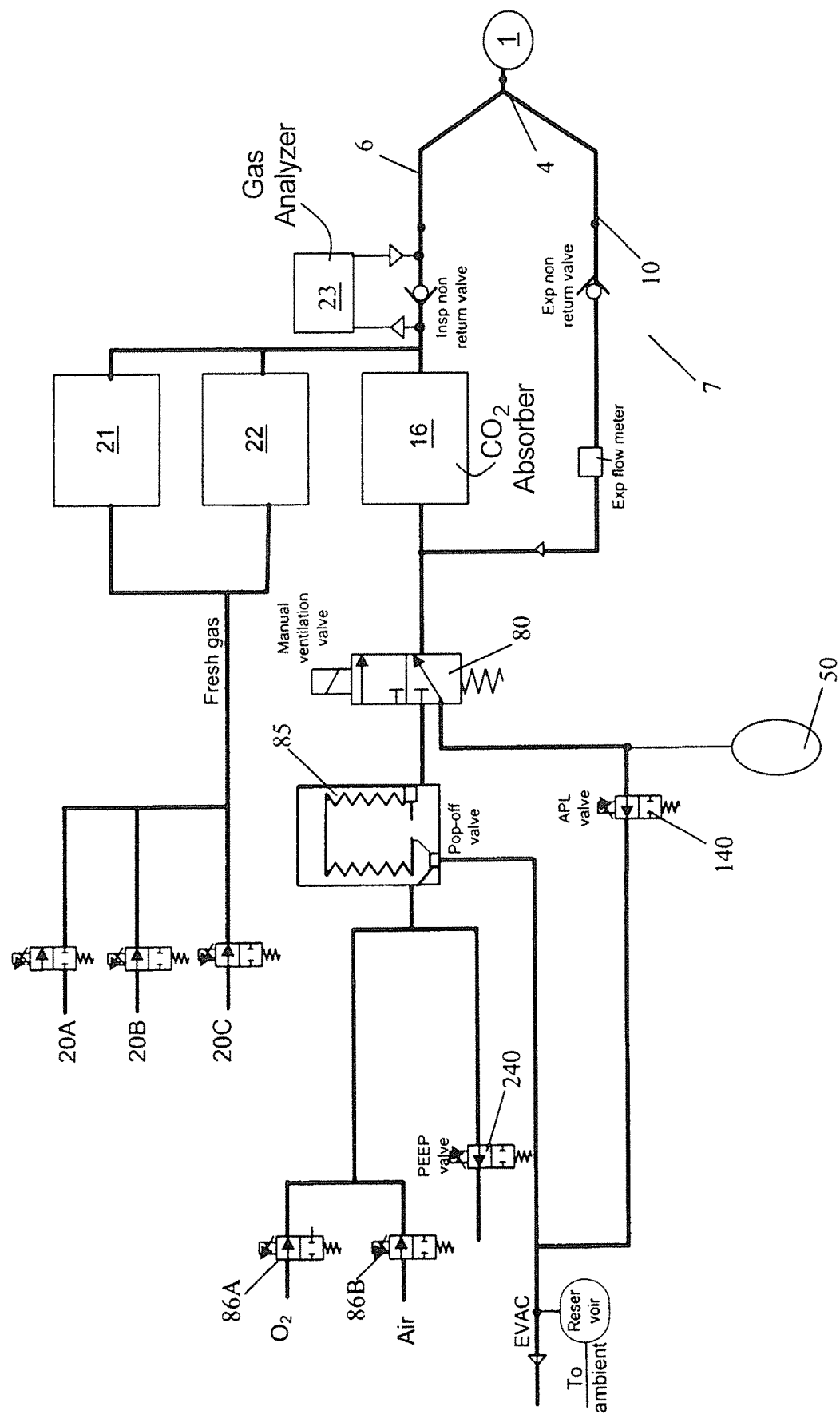
FIG. 2 is a schematic drawing of another anesthetic breathing apparatus.

FIG. 1 illustrates an anesthetic breathing apparatus in which some embodiments of the control method may be implemented. However, also other anesthesia breathing apparatuses that may fulfill the above-mentioned requirements may used for implementing embodiments of the control method. An alternative anesthetic breathing apparatus is illustrated in FIG. 2 and described further below.

FIG. 1 shows schematically, a breathing circuit of an anesthetic breathing apparatus, coupled to a circle system 7 with a mechanical ventilation system 53.

The airways of a patient 1 are connected to a patient tube 2 of a Y-piece 4 in a circular tubing system with an inspiration tube 6 provided with a first one-way valve 8 and an expiration tube 10 provided with a second one-way expiratory valve 12. A patient pressure sensor 74 is provided in the patient tube 2 connected to the Y-piece 4. Downstream the second one-way valve 12, in FIG. 1 in a clockwise direction along the circle system 7, a common expiration and inspiration line 14 is provided for the delivery of inspiration gas to the patient and evacuation of expiration gas from the patient. The common expiration and inspiration line 14 is coupled to the circle system 7 at a junction 15. Further along the circle system 7, the tubing passes through a CO2 absorber 16.

Downstream the CO2 absorber 16 a gas supply branch line 18 is provided to feed gas into the circle system 7 from a gas source. The gas supply branch line 18 is coupled to the circle system 7 at a junction 19.

The common expiration and inspiration line 14 may be provided with an adsorption filter 26 devised for adsorption and desorption of anesthetic and respiration gases to or from the patient. A breathing apparatus having an adsorption filter is disclosed in U.S. Pat. No. 5,471,979, which hereby is incorporated in its entirety by reference for all purposes. Alternatively a volume reflector may be provided, which is known as a Werner volume, such as described in U.S. Pat. No. 4,989,597, which hereby is incorporated herein in its entirety by reference for all purposes.

When having a volume reflector, it may replace adsorption filter 26, or be supplied additionally to the latter.

In FIG. 1 a gas flow selection unit 122 has the function of selecting fresh inhalation gas flow in a desired ratio through the first output branch 51 and/or through the second output branch 52 of the selection unit 122. Thus, the gas flow selection unit 122 may be actuated to a flow selection mode, in which the fresh inhalation gas is enabled to flow to the patient via the common expiration and inspiration line 14, when having an adsorption filter 26, or via the supply branch line 18 then bypassing the adsorption filter 26 as well as the CO2 absorber 16. In this manner a degree of re-breathing is adjustable by means of the gas flow selection unit 122, which will be described in more detail below.

In some embodiments using a bag in bottle system, the first output branch 51 of the gas flow selection unit 122 may be used to provide a driving gas flow for the bag in bottle system. Also, in a breathing apparatus comprising a volume reflector, the first output branch 51 may provide a drive gas flow for the volume reflector.

The fresh gas inhalation source may comprise multiple gas sources, such as an oxygen gas source 20A, and an air gas source 20B, as illustrated in FIG. 1. Additionally, the fresh inhalation gas source may comprise a nitrous oxide gas source 20C, such as shown in FIG. 2. A first anesthetic vaporizer 21 and a second anesthetic vaporizer 22 are fluidly connected to the fresh gas supply branch line 18 downstream the multiple gas sources and upstream the junction 19. In an embodiment, only one of the first and second anesthetic vaporizers 21, 22 are able to be activated at a time. The first and second anesthetic vaporizers 21, 22 are devised for vaporizing two different volatile anesthetic agents in the fresh gas flow that is delivered into the circle system 7 and with a flow of inspiratory gas to the patient 1. In an exemplifying breathing circuit the vaporizers 21, 22 may be injection type vaporizers.

A gas analyzer 23 is provided to analyze gas contents with an input of sample inspiratory gas in a sidestream. The sidestream is tapped downstream the junction 19 and upstream the first one-way valve 8 in the inspiratory branch. After analysis in gas analyzer 23, the sample gas is recirculated to the inspiratory flow downstream the first one-way valve 8 and upstream the Y-piece 4 in the inspiratory branch. A pressure sensor 70 is provided between the first one-way valve 8 and the recirculation point of the sample gas.

At the side turned opposite the circle system 7, the adsorption filter 26 of the common expiration and inspiration line 14 is coupled at a junction 24 to a first output branch line 51 from a gas flow selection unit 122. The gas flow selection unit 122 may be in the form of a bypass valve, switching input line 28 between either a first output branch 51 or a second output branch 52. However, gas flow selection unit 122 may in a practical implementation be a selection valve devised to control a ratio of gas flows between the first output branch 51 and the second output branch line 52. The second output branch line 52 of the gas flow selection unit 122 is coupled to the fresh gas supply line 18. At an input side, the gas flow selection unit 122 is coupled to the input line 28 connected to the fresh inhalation gas source.

The gas flow selection unit 122 is devised to select a flow route for the fresh inhalation gas via the supply branch line 18 and/or via the common expiration and inspiration line 14 downstream the adsorption filter 26 into the circle system 7. During inhalation, a gas flow ratio is controlled between the first output branch 51 and the second output branch line 52 in order to adjust a degree of rebreathing gas being pushed from adsorber 26 via line 14 into the breathing circuit.

An adsorption filter or a volume reflector is, amongst others, a storing element for one or more anesthetic agents, from which the latter are intermittently returned to the breathing circle. Thus, an anesthetic agent present in the breathing circle is retained in the breathing circle until it is eventually washed out. This is desired when only a single anesthetic agent is used during ventilation of the patient. However, when changing between different anesthetic agents, this may extend the time necessary for washing out an anesthetic agent present in the circle system to which the patient is connected.

Oxygen gas source 20A is coupled to an O2 inspiratory valve 30 that in its turn is connected to the input line 28 of the gas flow selection unit 122 at a blender 34. Similarly, air gas source 20B is coupled to an air inspiratory valve 32 that also is coupled to the input line 28 of the gas flow selection unit 122 at the blender 34. The O2 inspiratory valve 30 and the air inspiratory valve 32 are devised for adjusting the inlet flow and the proportions of the respective gases into the input line 28. Only O2 and air are shown, but nitrous oxide may also be used as is common in the art, see FIG. 2.

In FIG. 1 the gas flow selection unit 122 may have the function of selecting gas flow through the first output branch 51 and/or through the second output branch 52 of the gas flow selection unit 122, as described above. The distribution of the amounts of gas flow between the first output branch 51 and the second output branch 52 of the gas flow selection unit 122 is adjustable in real time.

Thus, the gas flow selection unit 122 may be actuated to a first flow selection mode where an amount of gas is enabled to flow to the patient via the common expiration and inspiration line 14, and/or via the supply branch line 18, as fresh gas, then bypassing the CO2 absorber 16. An arbitrary ratio may be adjusted between the first output branch 51 and the second output branch 52 of the gas flow selection unit 122.

An evacuation line 36 is connected to the common expiration and inspiration line 14 and to the mentioned first output branch line 51 at the junction 24. The evacuation line 36 leads via a flow meter 38 and a pressure sensor 76 to an expiratory valve 40 that is devised to control output of evacuated gas flow from the circle system 7 to a scavenging system 42 or to the atmosphere.

The mechanical ventilation system 53 and the expiratory valve 40 as well as other components may be parts of a per se known mechanical ventilator with a ventilation control system 56. The ventilation control system 56 may have a user input/output interface 58 with command input means and display means of a known type.

Also in a known manner, the ventilation control system 56 has a mechanical ventilation control (storage) medium 60 that is encoded with specifically designed computer program code for controlling the operation of the mechanical ventilation system 53 and its components via a symbolically shown control line 62. The mechanical ventilation control medium 60 enables venting of breathing gas from the mechanical ventilation system according to a set of predetermined control rules for controlling the expiratory valve 40 in accordance with ventilation mode requirements. In effect, the expiratory valve may in this connection be controlled to open or close at predefined pressure levels that occur in the tubing system. For instance, the control rules implement a mechanical ventilation mode comprising pressure control functions of the patient pressure. During expiration, a positive end expiratory pressure (PEEP) may be adjusted by the expiratory valve 40 at the end of the expiratory breathing phase, before the next inspiration phase starts. The expiratory valve 40 may also be operated to implement an adjustable pressure limit function during a manual ventilation mode. The expiratory valve 40 is usually closed during inspiration and controls the expiratory pressure level, and expiratory flow, during expiration.

The ventilation control system 56 further includes an anesthetic agent control unit 64. The anesthetic agent control unit 64 is devised to control the anesthetic vaporizers 21, 22 via the symbolically shown control line 66.

FIG. 2 illustrates another anesthetic breathing apparatus in which some embodiments of the control method may be implemented. Similar elements as in the anesthetic breathing apparatus shown in FIG. 1 are assigned similar reference signs in the anesthetic breathing apparatus of FIG. 2.

The anesthetic breathing apparatus in FIG. 2 includes a mechanical and a manual ventilation system that is capable of selectively drive breathing gas in a breathing circuit by means of a manual ventilation valve 80. The breathing circuit 7 of the anesthetic breathing apparatus illustrated in FIG. 2 includes a patient 1 circle with a CO2-absorber 16, one way valves, and the circle is connected to the manual ventilation valve and also to two selectably activatable vaporizers 21, 22 by means of which fresh gas from gas supply units 20A-C may be supplied to the circle. During mechanical ventilation, driving gas is supplied from gas sources through selection valves 86A, B to a bag in bottle unit 85 driving breathing gas inside the bag to and from the breathing circle 7, via the manual ventilation valve 80. The pressure of the breathing gas is controlled during expiration in that the driving gas flows through a PEEP valve 240. Excess gas, in the breathing circuit, is released through a POP-off valve in the bag in the bag-and-bottle unit 85, and further to an evacuation system.

During manual ventilation a manual bag 50 is used to drive breathing gas to and from the patient via the manual ventilation 80 valve and the patient circle. An APL-valve 140 is arranged limiting the pressure from the bag, said APL-valve may be a mechanical valve or an electronic APL valve, comprising a manually adjustable turning knob and a spring loaded valve. Excess gas is released through the APL-valve to an evacuation system.

In this embodiment, during mechanical ventilation, a degree of rebreathing is adjusted by choosing a desired degree of fresh gas (valves 20A-C) and breathing gas inside the bag to and from the breathing circle (selection valves 86A, B and the POP-off valve).

In some embodiments comprising a bag in bottle system, a continuous fresh gas flow or alternatively a pulsed fresh gas flow that is proportional a breathing cycle (e.g. either pressure controlled or flow controlled) may be provided, as is known in the art.

Figure 3:
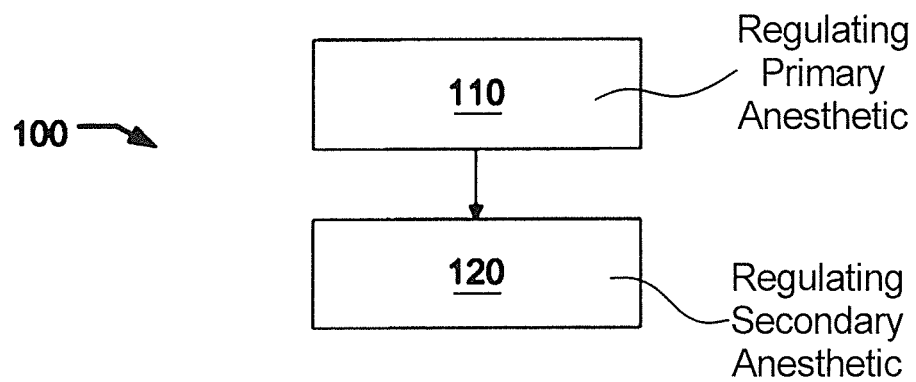
FIG. 3 is flow chart illustrating an embodiment of a method according to the invention.

FIG. 3 is flow chart illustrating an embodiment of a method according to the invention. The method 100 comprises the steps of:

a) regulating 110 a primary/new anesthetic agent added to a breathing circuit in such a manner that the concentration of the primary anesthetic agent, AA1, is adjusted to a set desired value of the concentration of the primary anesthetic agent, setAA1:

AA1=setAA1, and b) regulating 120 the concentration of a secondary agent, AA2, which is an anesthetic agent that previously was fed into the breathing circuit, in such a manner that it is equal to or less than a defined threshold level of the concentration of the secondary anesthetic agent, MAX_AA2:

AA2<=MAX_AA2.

Thus, re-breathing of the secondary anesthetic agent is reduced.

The steps of regulating 110, 120 may be implemented in the anesthetic breathing apparatus with reference to FIG. 1 by adjusting the degree of rebreathing. In more detail, the ratio of flow of fresh gas in line 18, including the primary/new anesthetic agent via one of selected vaporizers 21, 22, and the flow from the adsorber 26 via the common expiration and inspiration line 14 into the breathing circuit 7.

The steps of regulating 110, 120 may be implemented in the anesthetic breathing apparatus with reference to FIG. 2 by adjusting the degree of rebreathing. In more detail, a degree of rebreathing is in this embodiment adjusted by choosing a desired degree of fresh gas (valves 20A-C) and breathing gas inside the bag to and from the breathing circle (selection valves 86A, B and the POP-off valve).

An embodiment of the method is now illustrated with reference to FIG. 4. When changing the primary anesthetic agent, an anesthesiologist or an operator of the anesthesia breathing apparatus sets a desired concentration C of a new primary anesthetic agent that is desired to be delivered to the patient, at a time $t_0$. Concentration of the new primary agent in the breathing circuit, as measured by means of gas analyzer 23, will increase and be regulated to the set level. This is illustrated by curve 320 in FIG. 4.

Types or concentrations of anesthetic agents may be chosen via a man machine interface of the anesthetic breathing apparatus. In an embodiment only a single anesthetic agent may be chosen, a concentration thereof set, and the single anesthetic agent is delivered to the breathing circuit. Alternatively, or in addition, the operator may in some embodiments reduce the set concentration of the previous primary agent to a desired level, or turn it off. Alternatively, or in addition, the operator may in some embodiments choose to provide both the first and second anesthetic agent in desired concentrations, e.g. by selecting to activate both vaporizers 21, 22, each with one of the two different first and second anesthetic agent.

Figure 4:
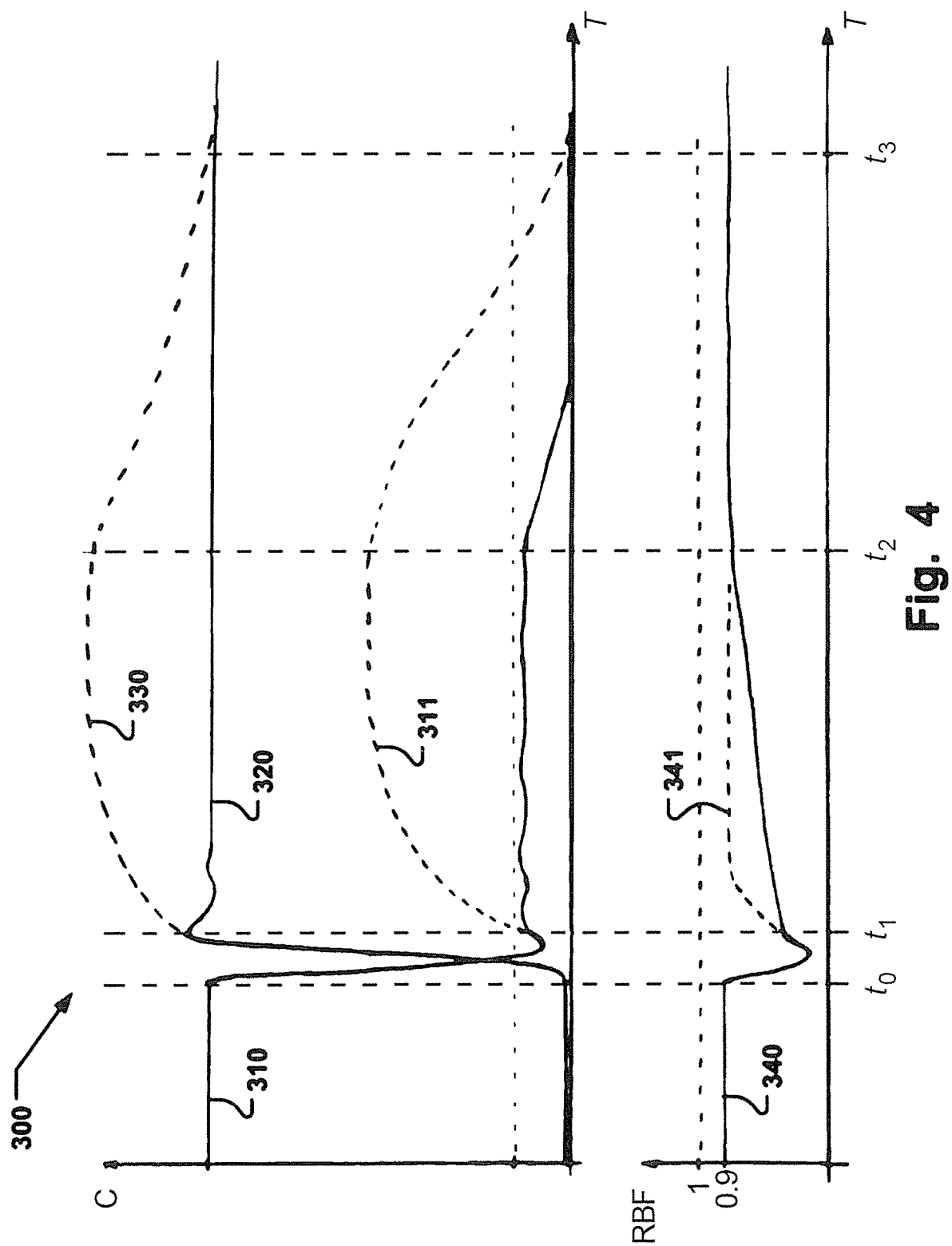
FIG. 4 is a graph illustrating a change of primary anesthetic agent that is controlled according to an embodiment of a method according to the invention.

The concentration C of the previous primary anesthetic agent, which is the secondary anesthetic agent after time $t_0$, is illustrated by curve 310 in FIG. 4.

Flushing of the breathing circuit is performed until time $t_1$, which is illustrated in the lower part of FIG. 4, where the re-breathing fraction (RBF) is shown on the same time scale T as the concentrations in the upper part of FIG. 4. A RBF of 1 corresponds to re-breathing 100% of the previously exhaled gases from the patient. A practical maximum RBF is approximately 0.9 as CO2 is absorbed in CO2 absorber 16 and replenished with fresh O2 via lines 14 or 18.

Conventionally, the RBF would be set to a high rate after the flush procedure, as illustrated by the dotted line 341. However in this case concentration of the previous primary anesthetic agent would increase even after the flush and replenishment with the new primary agent, as previous primary anesthetic agent dissolved in the blood of the patient would return to the breathing circuit via gas exhaled from the patient. This is illustrated by the dotted line 311. The total concentration of anesthetic agents that would be present in the breathing circuit in this case is illustrated by the dotted line 330. This is not desired, as explained above. By measuring gas concentrations and/or anesthetic agent concentrations in the tube connecting the Y-piece 4 to the patient 1 (not illustrated), both inhaled and exhaled concentration may in some embodiments be used for regulating anesthetic agents. For instance, a measured concentration of exhaled anesthetic agents may be used for determining an amount thereof stored in the breathing circle, minus potentially evacuated amounts thereof.

However, thanks to the regulating method, the RBF is adjusted accordingly, as shown by curve 340, in order to provide the desired regulation of the concentrations of the new primary agent AA1 and the previous primary agent AA2.

AA1 is thus regulated in a suitable manner such that AA1=setAA1. However, the regulation also takes into consideration and sees to that AA2<=MAX_AA2. This is a degree of freedom that optimizes the regulation method.

An increased degree of re-breathing of AA1 entails even an increased re-breathing of AA2. As AA2 is rinsed out of the breathing circuit, both into the patient and into the evacuation line, a higher degree of re-breathing is allowed. In an embodiment of the control method, the degree of re-breathing of anesthetic agents is limited such that AA2<=MAX_AA2. At a time $t_2$, all of the previous primary agent AA2 is rinsed out of the breathing circuit.

In order to minimize the consumption of anesthetic agent, the re-breathing is maximized, which entails an economical use of anesthetic agents fed into the breathing circuit from anesthetic vaporizers. Only a minimum of anesthetic agent is consumed or exhausted from anesthetic breathing apparatus, while ensuring patient safety and maintaining a desired level of anesthesia.

MAX_AA2 is chosen in such a manner that patient safety is ensured.

MAX_AA2 may be determined according to many different principles, for instance:
  as a fraction of setAA1, wherein the fraction may be fixed or variable and/or set by a user to a defined value;
  as a fraction of setAA1 in corresponding MAC values (explained below), wherein the fraction may be fixed or variable and/or set by a user to a defined value of the MAC number;
  as a fraction of AA1, wherein the fraction may be fixed or variable and/or set by a user to a defined value;
  as a fraction of AA1 in corresponding MAC values (explained below), wherein the fraction may be fixed or variable and/or set by a user to a defined value of the MAC number;
  as a level that is adjustable by a user, either as a MAC value or in absolute concentrations of an anesthetic agent;
  as a fraction of a mixed MAC total value, wherein the fraction may be fixed or variable and/or set by a user to a defined value of the mixed MAC total value, and wherein the mixed Mac total is calculated from the MAC value of the primary anesthetic agent and the MAC value of the secondary anesthetic agent;
  etc.

MAC is an abbreviation for "Minimum Alveolar Concentration" of anesthetic agents at a pressure of 1 atmosphere that produces immobility in 50 percent of those patient or animals exposed to a noxious stimulus. The MAC value is related to individual anatomical and/or physiological conditions, and is e.g. dependent on the age of the patient. The anesthetic agents mentioned above have in an example been found for a patient of 40 years of age: Halothane 0.8%, Enflurane 1.7%, Isoflurane 1.2%, Sevoflurane 2.1%, Desflurane 6.6%.

When having a mixture of several anesthetic agents, a mixed MAC may be calculated as a simple addition of the two MAC values of each of the anesthetic agents present in the mixture. In addition, a weighing of MAC efficiency parameters may contribute to the mixed MAC value, such as the type of anesthetic agent, patient related parameters, such as age, etc.

Figure 5:
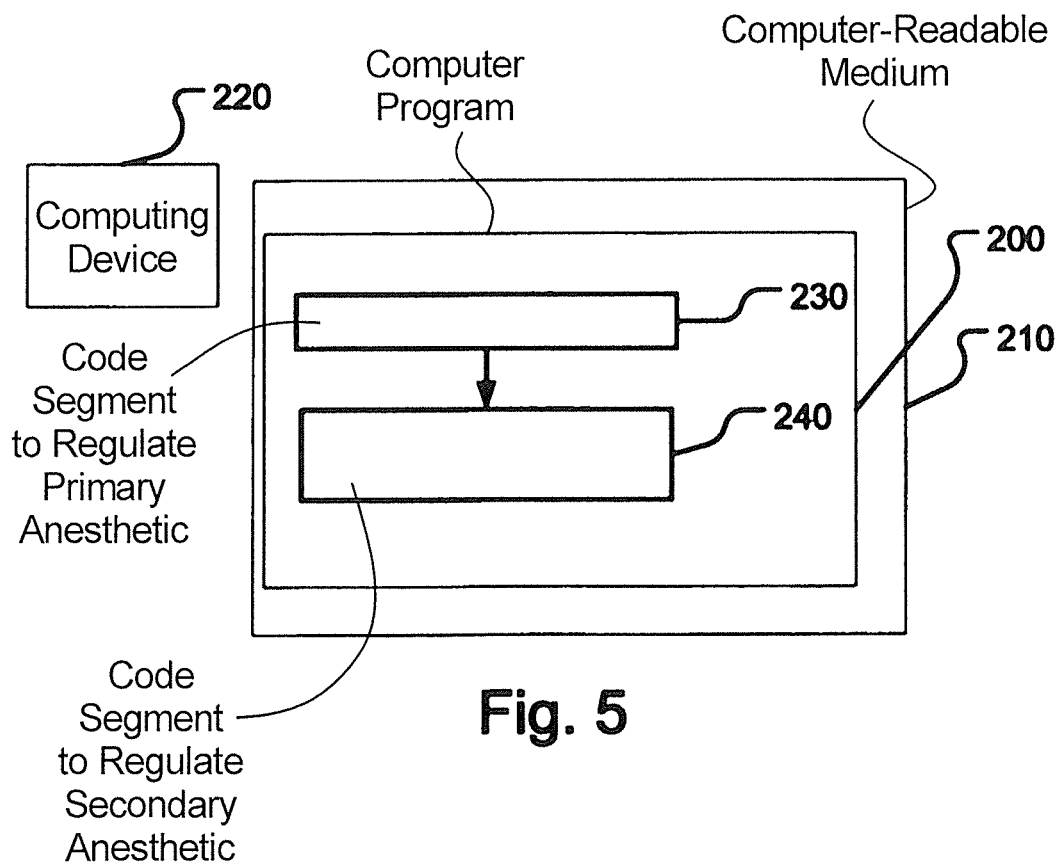
FIG. 5 is schematic drawing of a computer readable medium having embodied thereon an embodiment of a computer program executable by a computing device.

FIG. 5 is schematic drawing of a computer readable medium 210 having embodied thereon an embodiment of a computer program 200 executable by a computing device 220. The computing device 220 may be implemented in ventilation control system 56, or the anesthetic agent control unit 64 thereof. The computer program comprises a first code segment 230 for regulating a primary/new anesthetic agent added to a breathing circuit in such a manner that the concentration of the primary anesthetic agent, AA1, is adjusted to a set desired value of the concentration of the primary anesthetic agent, setAA1:AA1=setAA1, and a second code segment 240 for regulating the concentration of a secondary agent, AA2, which is an anesthetic agent that previously was fed into the breathing circuit, in such a manner that it is equal to or less than a defined threshold level of the concentration of the secondary anesthetic agent, MAX_AA2:AA2<=MAX_AA2. The level of the secondary anesthetic agent is in an embodiment controlled by a degree of re-breathing, as described above.

Multiple anesthetic agents may be regulated and controlled according to embodiments of the regulation method. In case more than two anesthetic agents are present in the breathing circuit the regulation method may be based on the following determinations:
  the secondary anesthetic agent is that anesthetic agent of the multiple anesthetic agents, which has the second highest concentration, and wherein the primary anesthetic agent has the highest concentration;
  the secondary anesthetic agent is that anesthetic agent of the multiple anesthetic agents, which has the second highest MAC value, and wherein the primary anesthetic agent has the highest MAC value;
  the secondary anesthetic agent is defined as the sum of all remaining anesthetic agents that are present in addition to the primary anesthetic agent that has the highest concentration;
  the secondary anesthetic agent is defined as the sum of all MAC values of the remaining anesthetic agents that are present in addition to the primary anesthetic agent that has the highest MAC value; etc.

Dosage of a mixture of anesthetic agents to the breathing circuit 7, e.g. at junction 19, may be provided by controlling an output of multiple vaporizers, e.g. vaporizers 21, 22, dispensing different anesthetic agents.

In this manner, a combined dose may be controlled by some embodiments of the method of regulating multiple anesthetic agents in a breathing circuit of an anesthetic breathing apparatus.

For instance, a combined MAC may be set by a user of an anesthetic breathing apparatus as the desired MAC value of the primary anesthetic agent to be delivered to patient 1:

$$\text{set\_MAC}=\text{MAC}(\text{AA1\_}a)+\text{MAC}(\text{AA1\_}b),$$

wherein AA1_a is the first primary anesthetic agent and AA1_b is the second primary anesthetic agent.

In addition, a ratio between AA1_a and AA1_b may be adjustable with individual factors, e.g.
  i) Set_MAC=$K_a^{-1}$*MAC (AA1_a)
  Set_MAC=$K_b^{-1}$*MAC (AA1_b),
  wherein $K_a+K_b=1$.
  Or ii) AA1_a=$K_a$ (AA1_a+AA1_b)
  AA1_b=$K_b$ (AA1_a+AA1_b)),
  wherein $K_a+K_b=1$.

In the above, the user provides and inputs a desired ratio in MAC values according to i); or provides and inputs a desired ratio of absolute concentrations according to ii); in both cases for the first primary anesthetic agent and the second primary anesthetic agent. This means that the desired ratio or distribution of the first primary anesthetic agent the second primary anesthetic agent is provided and input by the user for the control method that in turn implements the described regulation in order to achieve the desired input in the breathing circle 7 in an advantageous way.

An example is now given to illustrate this principle. For instance, a user may input a desired MAC value of the primary anesthetic agent to 1.2, set_MAC=1.2. Furthermore, the user may input that 70% Sevoflurane and 30% Isoflurane are to be used. The anesthetic breathing apparatus 5 has in this example two anesthetic vaporizers, e.g. vaporizers 21, 22. The first vaporizer 21 may be a vaporizer delivering Sevoflurane and the second vaporizer 22 may be a vaporizer delivering Isoflurane, wherein 70% of the dose are to be delivered from the first vaporizer, and 30% of the dose are to be delivered from the second vaporizer 22. The distribution ratio may in this example be calculated as 1.2*0.7=MAC(SEV), which result in approximately 1.6% Sevoflurane to be delivered by vaporizer 21, and 1.2*0.3=MAC(ISO), which result in approximately 0.4% Isoflurane to be delivered by vaporizer 22.

The mixed MAC value may also be a combination of a mix of multiple primary anesthetic agents (first, second, . . . primary anesthetic agents) and a mixed MAC of multiple secondary anesthetic agents (first, second, secondary anesthetic agents), resulting in a mixed MAC_total value, which might be used as a control parameter for the method of regulating multiple anesthetic agents in a breathing circuit of an anesthetic breathing apparatus.

As mentioned above, when having a mixture of several anesthetic agents, a mixed MAC may be calculated in various ways, e.g. as an addition of the several MAC values of each of the anesthetic agents present in the mixture; or by weighing of MAC efficiency parameters, etc.

Figure 6A:
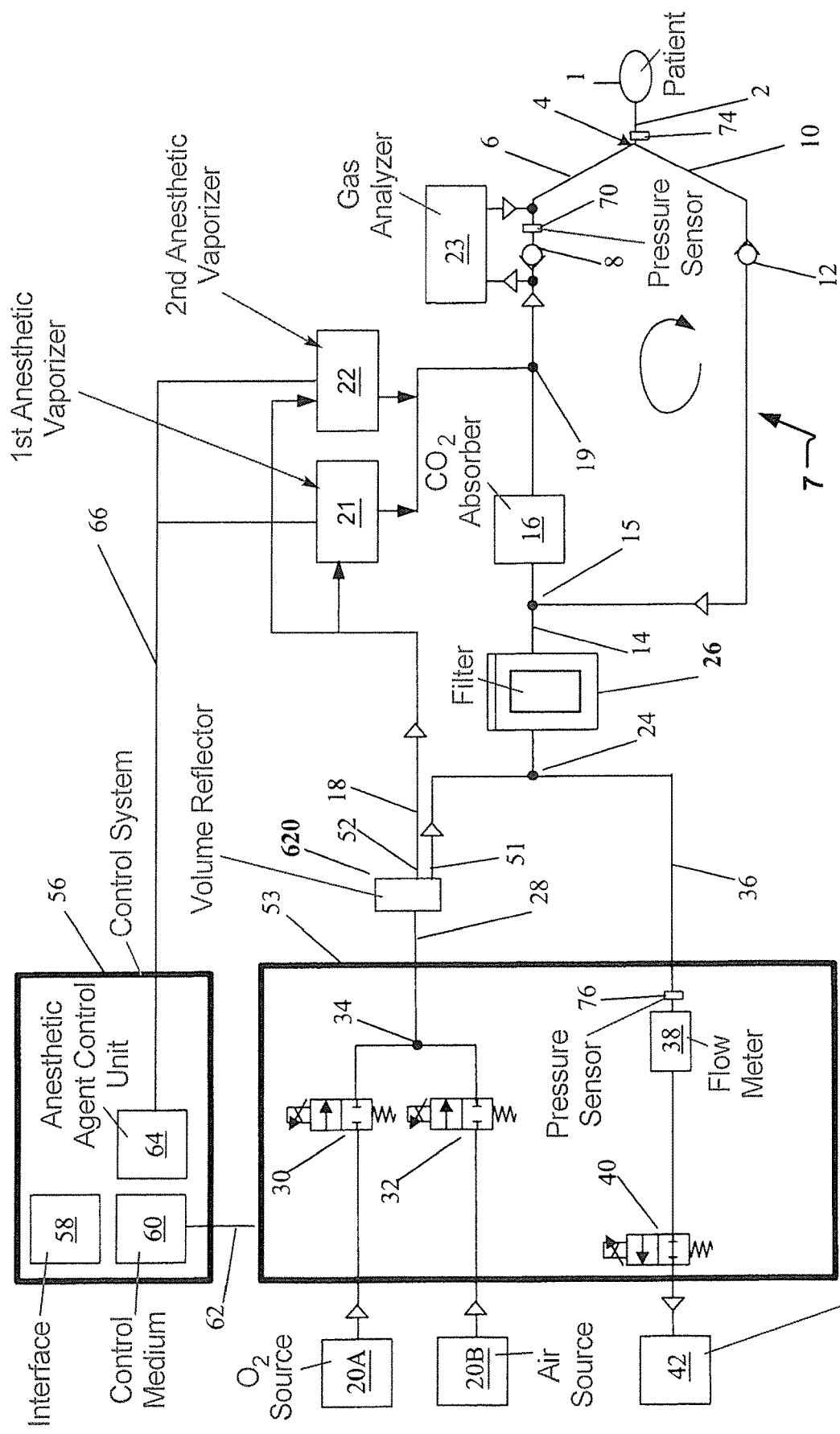
FIGS. 6a, 6b, and 6c are schematic illustrations of anesthetic breathing apparatuses having a continuously adjustable degree of re-breathing including a shunt valve (FIG. 6a); pulse width modulated (PWM) valves (FIG. 6b); and a "multi-pack" of valves, e.g. a "four pack" of valves; respectively.
Figure 6B:
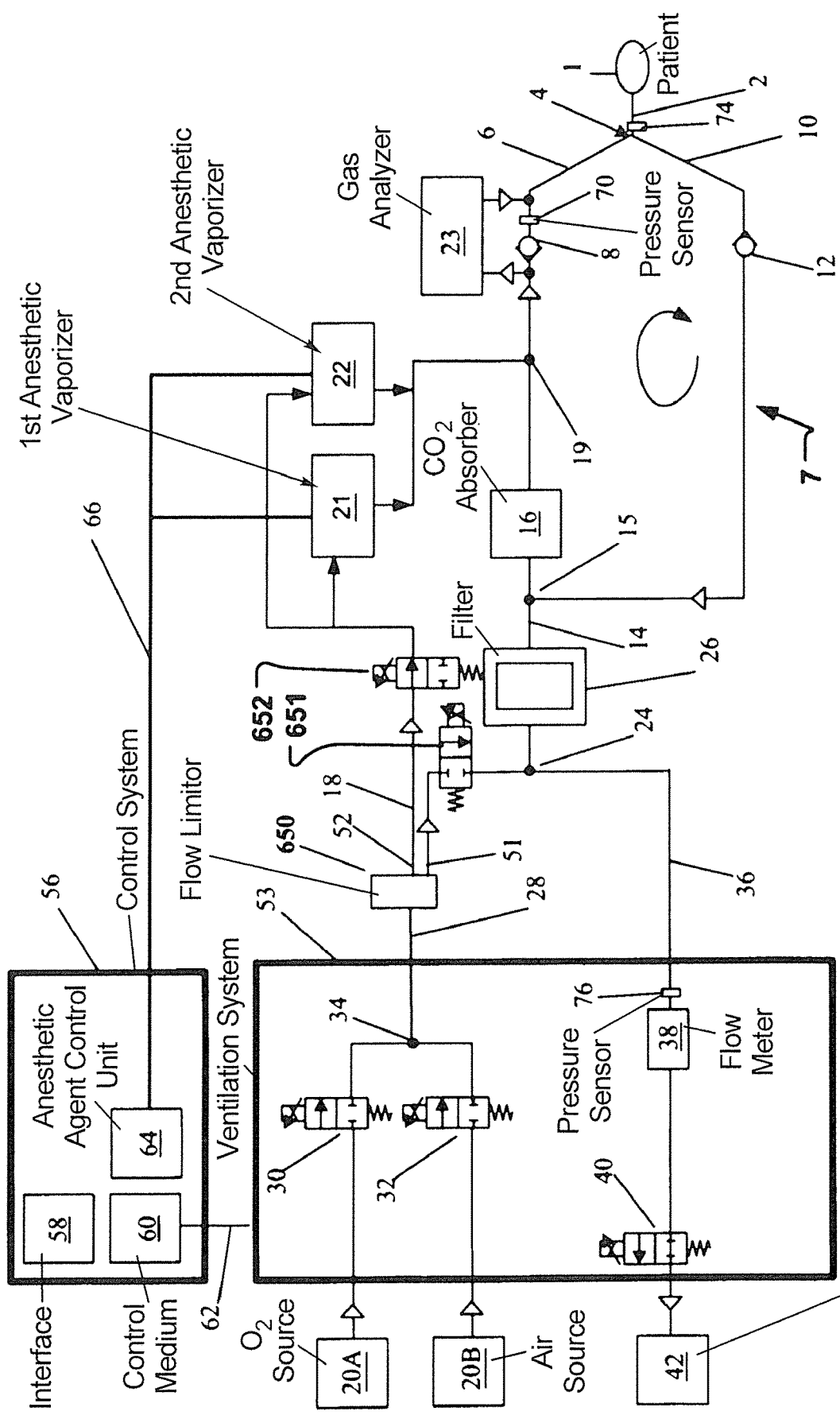
Figure 6C:
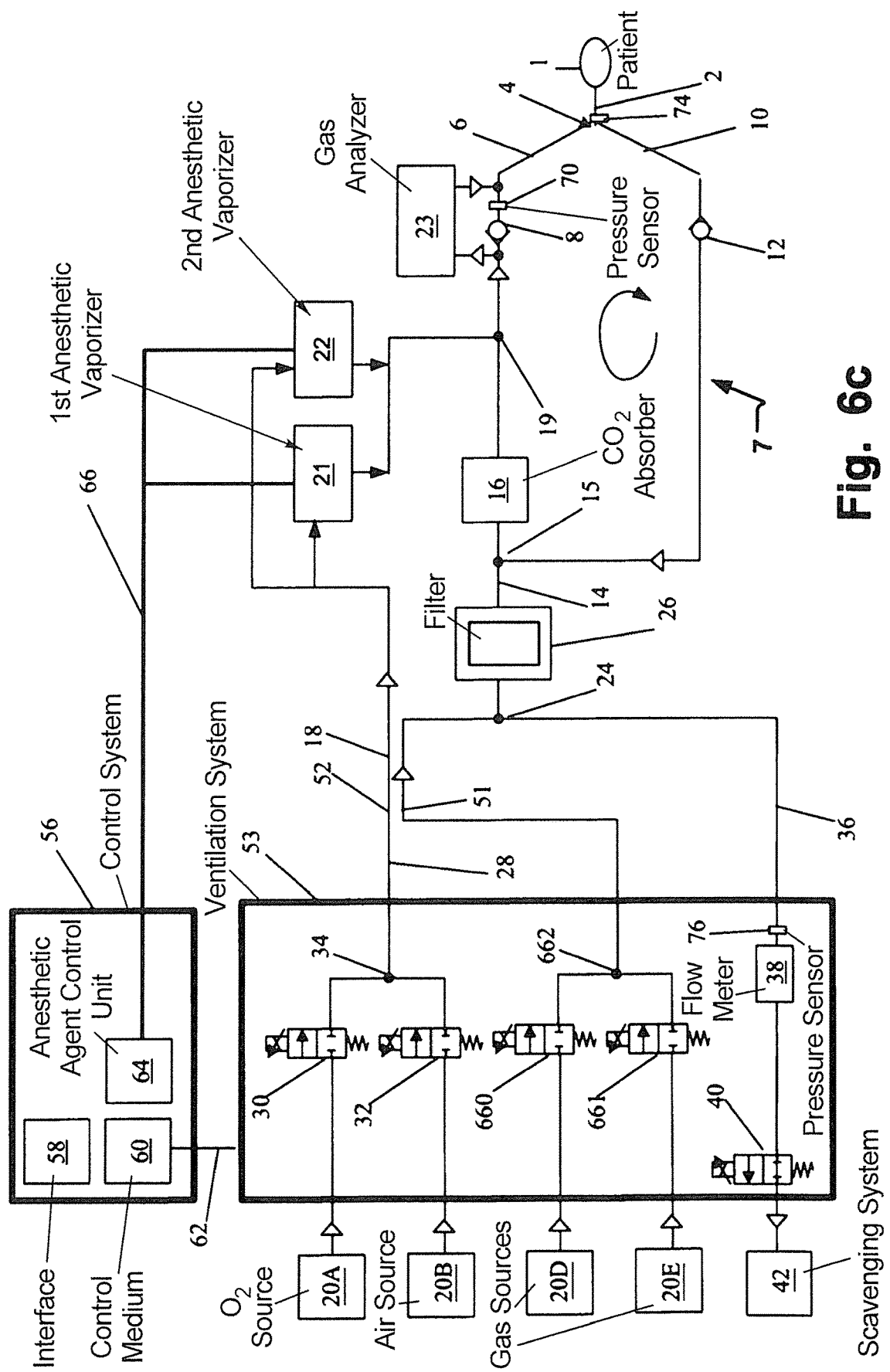

FIGS. 6a, 6b, and 6c are schematic illustrations of anesthetic breathing apparatuses having a continuously adjustable degree of re-breathing including a shunt valve (FIG. 6a); pulse width modulated (PWM) valves (FIG. 6b); and a "multi-pack" of valves, e.g. a "four pack" of valves; respectively. The basic set-up of the anesthetic breathing apparatuses in FIGS. 6a to 6c is similar to that described above with reference to FIG. 1. Similar elements are shown with the same reference numbers and are not explained in detail in addition to the description given above with reference to FIG. 1. The anesthetic breathing apparatuses in FIGS. 6a to 6c mainly differ from that shown in FIG. 1 by specific implementations of the gas flow selection unit 122 for controlling a degree of re-breathing to the circle system 7 and patient 1. All the anesthetic breathing apparatuses described below in more detail with reference to FIGS. 6a to 6c may implement embodiments of the above described methods of regulating multiple anesthetic agents in a breathing circuit of an anesthetic breathing apparatus.

In more detail an anesthetic breathing apparatus having a continuously adjustable degree of re-breathing including a shunt valve 620 is shown in FIG. 6a. Furthermore, the anesthetic breathing apparatus comprises a volume reflector and/or adsorption filter (26 not shown). The shunt valve 620 is configured and controllable such that it continuously distributes the gas flow between the first output branch 51 and the second output branch 52.

For instance by distributing the entire flow of gas from junction 34 to the second output branch 52, the re-breathing fraction (RBF) is zero, i.e. the entire flow of inspiratory gas into patient 1 originates from this line, including an addition of one or more anesthetic agents from vaporizers 21, 22.

In order to increase the RBF, a portion of the flow of gas from junction 34 is distributed to the first output branch 51, pushing gas from volume reflector and/or adsorption filter 26 into the breathing circuit, which at junction 19 is blended with gas originating from the second output line 52 and conveyed further into the patient 1. The gas pushed from the volume reflector and/or adsorption filter 26 into the breathing circuit 7 is composed of previously exhaled patient gas, e.g. including one or more anesthetic agents. Hence, this previously exhaled patient gas is provided for re-breathing to the patient, after passing through the $CO_2$ absorber 16.

With reference to FIG. 6b an anesthetic breathing apparatus having a continuously adjustable degree of re-breathing by means of pulse width modulated (PWM) valves is shown in more detail. In contrast to the shunt valve 620, which might be practically difficult to implement, e.g. due to sealing issues, a double set of PWM valves 651, 651 are provided. Each of the PWM valves 651, 651 is an on-off valve. The PWM valves 651, 651 are driven by pulsed signals, wherein the length of the pulses determines a ratio of opening of the valve. In this manner, the PWM valves 651, 651 continuously distribute the gas flow originating from blender 34 between the first output branch 51 and the second output branch 52. The total gas flow comprises of the gas flows through the first output branch 51 and the second output branch 52 is determined by a flow limiter or valve 650 adjustable to a desired flow rate.

The common expiration and inspiration line 14, provided with an adsorption filter 26 devised for adsorption and desorption of anesthetic and respiration gases to or from the patient, thus provides gas for re-breathing to patient one in a determined ratio with gas originating from the second output line 52 via one or more vaporizers 21, 22.

Alternatively, the second output line 52 may be directed to junction 15 instead of junction 19 as illustrated. Provided that the pulse frequency of the signals controlling the PWM valves 651, 651 is sufficiently large, the gas fractions entering the breathing circle 7 during inspiration are blended sufficiently before reaching the gas analyzer 23 or patient 1.

Hence, in this embodiment, an RBF is determined by a ratio of the PWM signals controlling the degree of opening of PWM valves 651, 652.

The PWM valves 651, 652 may be controlled in counter phase, such that either the one or the other of PWM valves 651, 652 provides gas to the breathing circuit 7 at a given time.

The RBF is in this embodiment controlled by the PWM signal to the PWM valves 651, 652.

With reference to FIG. 6c, an anesthetic breathing apparatus having a continuously adjustable degree of re-breathing by means of a "four pack" of valves is now described in more detail.

The mechanical ventilation system 53 comprises in this embodiment one or more additional inspiratory valves 660, 661, also called gas modules. The inspiratory valves may be highly sophisticated sub-systems of the anesthetic breathing apparatus, having an inherent high precision gas flow and pressure control.

In addition to the breathing apparatus described with reference to FIG. 1, the fresh gas inhalation source may comprise further gas sources, such as gas source 20D, and gas source 20E, as illustrated in FIG. 6c. Additionally, the fresh inhalation gas source may have a nitrous oxide gas source. Alternatively, or in addition, the oxygen gas source 20A may be coupled to the input of inspiratory valve 660, and the air gas source 20B may be coupled to the input of the inspiratory valve 661. In this case, the gas sources 20D, 20E may be omitted and the inspiratory valves 30, 660, and 32, 661, may be driven from single gas sources respectively. The multiple inspiratory valves 30, 32, 660, 661 are called "multi-packs" of valves, in the present example a "four-pack" of inspiratory valves.

The gas flow selection unit 122 is in this case implemented by the inspiratory valves 30, 32 and one or more additional inspiratory valves 660, 661, i.e. the "multi-pack" of inspiratory valves. The inspiratory valves 660, 661 may be controlled to provide a desired oxygen concentration at a junction or blender 662. Only O2 and air are shown, but nitrous oxide may also be used. Alternatively only one of inspiratory valves 660, 661 is implemented in a "three-pack" of inspiratory valves.

Gas flow from inspiratory valves 660, 661 via blender 662 is provided to the first output line 51. Gas flow from inspiratory valves 30, 32 via blender 34 is provided to the first second line 51. A ratio of total flow between the first output line 51 and the second output line 52 is adjustable by suitably controlling a portion of gas flow via blender 34 and blender 662 respectively. In this manner, the distribution of the amounts of gas flow between the first output branch 51 and the second output branch 52 is adjustable in real time.

Thus, the "multi-pack" of inspiratory valves may be actuated to a first flow selection mode where an amount of gas is enabled to flow to the patient via the common expiration and inspiration line 14, and/or via the supply branch line 18, as fresh gas, then bypassing the CO2 absorber 16. An arbitrary ratio may be adjusted between the first output branch 51 and the second output branch 52 of the gas flow selection unit 122 by controlling the inspiratory valves 30, 32, 660, 661 in desired manner. Thus, a desired RBF is adjustable by controlling the "multi-pack" of inspiratory valves as described above.

As a consequence of gas flows being completely independently controllable by the individual inspiratory valves of "multi-packs", the anesthetic breathing apparatus may provide complete or partial breathing cycles. Alternatively, a conventional system with a continuous fresh gas flow may be simulated, including a virtual bag in bottle system, as shown in FIG. 2.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

I claim as my invention:

1. A system comprised in an anesthetic breathing apparatus, for regulating multiple anesthetic agents in a breathing circuit of said anesthetic breathing apparatus, said system comprising:
   a gas analyzer configured to measure concentrations of two or more anesthetic agents simultaneously;
   at least one vaporizer configured to add anesthetic agent(s) to a fresh gas flow; and
   a control system configured to regulate a dose of at least one primary anesthetic agent added to said breathing circuit via said fresh gas flow and a dose of at least one secondary anesthetic agent already present in said breathing circuit by controlling a ratio of re-breathed gas and fresh gas in said breathing circuit,
   wherein said at least one primary anesthetic agent and at least one secondary anesthetic agent are volatile anesthetic agents, said at least one primary anesthetic agent was previously not present in the breathing circuit, and said ratio ensures that an effect of mixed anesthetic agents is on a controlled level.

2. The system according to claim 1 wherein said control system is configured to regulate said at least one primary anesthetic agent added to said breathing circuit via said fresh gas flow to a set dose of said at least one primary anesthetic agent, and regulating at least one secondary anesthetic agent already present in said breathing circuit, to a dose of said at least one secondary anesthetic agent that it is equal to or less than a defined dose of said at least one secondary anesthetic agent.

3. The system according to claim 2, wherein said control system is configured to adjust a degree of re-breathing gas from said breathing circuit to a patient fluidly connected thereto in dependence of said set dose of said at least one primary anesthetic agent and said defined dose of said at least one secondary anesthetic agent.

4. The system according to claim 1, wherein said at least one primary anesthetic agent comprises a first primary anesthetic agent and a second primary anesthetic agent and wherein said control system is configured to regulate a dose of said first primary anesthetic agent and a dose of said second primary anesthetic agent added to said breathing circuit.

5. The system according to claim 1, wherein said at least one secondary anesthetic agent is an anesthetic agent among multiple anesthetic agents present in said breathing circuit, which has the second highest concentration, and wherein said at least one primary anesthetic agent is an anesthetic agent, among said multiple anesthetic agents present in said breathing circuit, which has the highest concentration.

6. The system according to claim 1, wherein said at least one secondary anesthetic agent is an anesthetic agent among multiple anesthetic agents in said breathing circuit, which has the second highest Minimum Alveolar Concentration (MAC) value, and wherein said at least one primary anesthetic agent is an anesthetic agent, among said multiple anesthetic agents, which has the highest MAC value.

7. The system according to claim 6, wherein said at least one secondary anesthetic agent is a sum of concentrations of remaining multiple anesthetic agents that are present in addition to the at least one primary anesthetic agent that has the highest concentration in said breathing circuit.

8. The system according to claim 6, wherein said at least one secondary anesthetic agent is a sum of MAC values of remaining multiple anesthetic agents that are present in addition to the at least one primary anesthetic agent that has the highest MAC value in said breathing circuit.

9. The system according to claim 1, wherein said dose of the at least one secondary anesthetic agent is determined as a fraction of said dose of said at least one primary anesthetic agent, wherein said fraction is fixed or variable.

10. The system according to claim 1, wherein said dose of the at least one secondary anesthetic agent is determined as a fraction of a Minimum Alveolar Concentration (MAC) value of said at least one primary anesthetic agent, wherein said fraction is fixed or variable.

11. The system according to claim 1, wherein said dose of the at least one secondary anesthetic agent is determined as a fraction of a mixed Minimum Alveolar Concentration (MAC) total value, wherein the fraction is fixed or variable, and wherein the mixed MAC total is calculated from the MAC value of the at least one primary anesthetic agent and the MAC value of the at least one secondary anesthetic agent.

12. The system according to claim 1, wherein a Minimum Alveolar Concentration (MAC) value of said at least one primary anesthetic agent and a MAC value of said at least one secondary anesthetic agent are combined into a mixed MAC total value.

13. The system according to claim 1, wherein the control system is configured to selectively regulate a concentration of the at least one primary anesthetic agent and a concentration of the at least one secondary anesthetic agent simultaneously for at least a portion of time.

14. The system according to claim 13, wherein the at least one vaporizer comprises a first vaporizer configured to add said at least one primary anesthetic agent and a second vaporizer configured to add said at least one secondary anesthetic agent, and the control system is configured to selectively activate the first vaporizer and the second vaporizer to regulate the concentration of the at least one primary anesthetic agent and the concentration of the at least one secondary anesthetic agent.

15. A non-transitory, computer-readable data storage medium encoded with programming instructions, said storage medium being loaded into a control computer that is configured to operate a breathing circuit of an anesthetic breathing apparatus, and said programming instructions causing said control computer to execute steps comprising:

regulate at least one primary anesthetic agent added to the breathing circuit via a fresh gas flow; and regulate at least one secondary anesthetic agent that is already present in said breathing circuit by controlling a ratio of re-breathed gas and fresh gas in said breathing circuit, wherein said at least one primary anesthetic agent and said at least one secondary anesthetic agent are volatile anesthetic agents, said at least one primary anesthetic agent was previously not present in the breathing circuit, and said ratio ensures that an effect of mixed anesthetic agents is on a controlled level.

* * * * *